(12) United States Patent
Morikawa et al.

(10) Patent No.: US 6,191,327 B1
(45) Date of Patent: Feb. 20, 2001

(54) METHOD FOR PRODUCING DICHLOROPENTAFLUOROPROPANES

(75) Inventors: Shinsuke Morikawa; Keiichi Ohnishi; Hidekazu Okamoto; Toshihiro Tanuma, all of Yokohama (JP)

(73) Assignee: Asahi Glass Company Ltd., Tokyo (JP)

( * ) Notice: Under 35 U.S.C. 154(b), the term of this patent shall be extended for 0 days.

(21) Appl. No.: 08/157,429

(22) Filed: Nov. 26, 1993

Related U.S. Application Data

(63) Continuation of application No. 07/915,819, filed on Jul. 27, 1992, now abandoned.

(30) Foreign Application Priority Data

Nov. 27, 1990 (JP) ................................................ 2-321221
Jun. 3, 1991 (JP) ................................................ 3-160099
Nov. 27, 1991 (WO) ................................. PCT/JP91/01627

(51) Int. Cl.[7] .................................................. C07C 21/18
(52) U.S. Cl. ............................................................. 570/172
(58) Field of Search ............................................... 570/172

(56) References Cited

U.S. PATENT DOCUMENTS 3,381,042 * 4/1968 Yale ...................................... 570/172
3,795,710 * 3/1974 Seignevrin ............................ 570/172
5,185,483 * 2/1993 Aoyama et al. ...................... 570/172
5,264,639   11/1993 Morikawa et al. .

FOREIGN PATENT DOCUMENTS

0421322 * 4/1991 (EP) ...................................... 570/172
3-118338   5/1991 (JP) .
3-178940   8/1991 (JP) .
9101287 * 2/1991 (WO) ................................... 570/172
9108183 * 6/1991 (WO) ................................... 570/172

* cited by examiner

*Primary Examiner*—Alan Siegel
(74) *Attorney, Agent, or Firm*—Oblon, Spivak, McClelland, Maier & Neustadt P.C.

(57) ABSTRACT

The present invention relates to a simple method for producing 3,3-dichloro-1,1,1,2,2-pentafluoropropane (R225ca) and 1,3-dichloro-1,1,2,2,3-pentafluoropropane (R225cb) in good yield and at high selectivity by reacting tetrafluoroethylene ($C_2F_4$) and dichlorofluoromethane (R21) in the presence of a certain specific catalyst.

The specific catalyst in the present invention is (1) a catalyst comprising halogenated oxide containing at least one element of Group 4, Group 5 and Group 13 such as Ti, Zr, Hf, V, B and Ga, or (2) a catalyst comprising halogenated oxide containing at least one element selected from Group 4, Group 5 and Group 13 such as Ti, Zr, Hf, V, B, Al and Ga and at least one element selected from Group 2, Group 6, Group 12 and Group 14 such as Ba, W, Zn, Si, Bi and P.

29 Claims, No Drawings

METHOD FOR PRODUCING DICHLOROPENTAFLUOROPROPANES

This application is a Continuation of application Ser. No. 07/915,819, filed on Jul. 27, 1992, now abandoned.

TECHNICAL FIELD

The present invention relates to a process for producing 3,3-dichloro-1,1,1,2,2-pentafluoropropane (hereinafter sometimes referred to simply as R225ca) and 1,3-dichloro-1,1,2,2,3-pentafluoropropane (hereinafter sometimes referred to simply as R225cb).

BACKGROUND ART

Hydrogen-containing chlorofluoropropanes such as R225ca and R225cb are expected to be useful as blowing agents, refrigerants or cleaning agents, like conventional chlorofluorocarbons.

Heretofore, a method for synthesizing R225ca and R225cb by the addition reaction of tetrafluoroethylene (hereinafter sometimes referred to simply as 4F) with dichlorofluoromethane (hereinafter sometimes referred to simply as R21) in the presence of an aluminum chloride catalyst, as shown by the following formula.

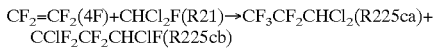

CF$_2$=CF$_2$(4F)+CHCl$_2$F(R21)→CF$_3$CF$_2$CHCl$_2$(R225ca)+ CClF$_2$CF$_2$CHClF(R225cb)

[see 1) U.S. Pat. No. 2,462,402 (Du Pont), 1949, 2) D. Coffman, et al., Journal of American Chemical Society, 71,979 (1949), 3) O. Paleta, et al., Collect. Czech. Chem. Commun., 36, 1867 (1971)]

Thereafter, an improved synthesis of R225ca and R225cb employing aluminum chloride or halogenated aluminum oxide alone, as a catalyst in the above reaction, has been proposed.
[see 4) Japanese Unexamined Patent Publication No. 118338/1991 (Daikin), 5) Japanese Unexamined Patent Publication No. 178940/1991 (Daikin), 6) EP-0-421322-A1 (Daikin)]

Methods 1), 2) and 3) employing an aluminum chloride catalyst, have a difficulty that chloroform which forms azeotrope with the desired products, will be formed in a large amount as a by-product, and dichloropentafluoropropane isomers which are hardly separable by a usual method such as distillation because their boiling points are close to those of the desired products, will be formed as by-products. Such isomers include 2,2-dichloro-1,1,1,3,3-pentafluoropropane (hereinafter sometimes referred simply as R225aa) and 2,3-dichloro-1,1,1,2,3-pentafluoropropane (hereinafter sometimes referred to simply as R225ba). Accordingly, they have a drawback that a multi-stage purification process is required in order to obtain highly pure R225ca and R225cb, and it has been desired to suppress the formation of such by-products.

Further, in the improved methods 4), 5) and 6), formation of chloroform is suppressed to some extent, but no improvement has been made with respect to the formation of R225aa and R225ba as by-products.

DISCLOSURE OF THE INVENTION

The present inventors have conducted an extensive study for a method for efficiently producing R225ca and R225cb and as a result, have found it possible to form R225ca and R225cb in good yield substantially without formation of R225aa and R225ba by using a catalyst comprising halogenated oxide containing at least one element selected from Group 4, Group 5 and Group 13 (excluding, however, halogenated aluminum oxide alone). Further, even with a halogenated aluminum oxide, it is possible to suppress formation of R225aa and R225ba effectively by converting it to a composite halogenated oxide with other elements. Further, it has been found that R225ca and R225cb can be obtained in good yield while suppressing formation of chloroform as a by-product, by adding the excess amount of 4F to R21 when 4F and R21 are reacted.

Firstly, the present invention provides a novel method for producing 3,3-dichloro-1,1,1,2,2-pentafluoropropane and 1,3-dichloro-1,1,2,2,3-pentafluoropropane, which comprises reacting tetrafluoroethylene with dichlorofluoromethane in the presence of a catalyst comprising halogenated oxide containing at least one element selected from Group 4, Group 5 and Group 13 (excluding a halogenated aluminum oxide alone).

Further, the present invention provides a novel method for producing 3,3-dichloro-1,1,1,2,2-pentafluoropropane and 1,3-dichloro-1,1,2,2,3-pentafluoropropane, which comprises reacting tetrafluoroethylene with dichlorofluoromethane in the presence of a catalyst comprising halogenated oxide containing at least one element selected from Group 4, Group 5 and Group 13 and at least one element selected from Group 2, Group 6, Group 12, Group 14 and Group 15.

The catalyst comprising halogenated oxide containing at least one member selected from Group 4, Group 5 and Group 13 in the present invention, can be represented by the general formula (1):

MX$_p$O$_q$            (1)

wherein M is at least one element selected from Group 4, Group 5 and Group 13, and X is at least one element selected from F, Cl, Br and I, and 0<p<5, 0<q<2.5 and 3≦p+2q<8.

X in the above general formula (1) is preferably at least one or two elements selected from F and Cl. It is essential that component M contains an element selected from Group 4, Group 5 and Group 13. However, a case where component M is aluminum alone is excluded, since in such a case, R225aa and R225ba will be produced in a large amount as by-products.

Elements selected from Group 4, Group 5 and Group 13 may be used alone or as a mixture of two or more of them. It is considered that in halogenated oxide in which two or more elements selected from Group 4, Group 5 and Group 13 coexist, crystal lattice defects will be introduced, whereby the reaction activity will increase, and by introducing other elements with electronically different states, electronical states of the catalyst can be changed, whereby the activity of the catalyst can readily be controlled. Accordingly, in the present invention, it is preferred to use two or more elements selected from Group 4, Group 5 and Group 13, as component M. In such a case, the mixing proportions are not particularly limited, and the respective elements may be mixed in various proportions within a range from 1 wt % to 99 wt %.

For the same reason, it is possible to use, as component M, either an element or elements selected from Group 4, Group 5 and Group 13 in combination with at least one other element. Such other element is not particularly limited, but element selected from Group 2, Group 6, Group 12, Group 14 and Group 15 is preferred. Also in this case, the mixing proportions are not particularly limited, and the former and latter elements may be mixed in proportions within a range from 1 wt % to 99 wt %.

In a case where aluminum is contained as component M in the general formula (1), formation of R225aa and R225ba as by-products can be suppressed by an addition of other element. Such other element is not particularly limited, but an element selected from Group 4, Group 5 and Group 13 except for aluminum and an element selected from Group 2, Group 6, Group 12, Group 14 and Group 15, is particularly preferred. In such a case, the mixing proportions of aluminum and other element may be at any optional proportions. However, in order to suppress the formation of R225aa and R225ba effectively, it is preferred to control the mixing porportion of aluminum preferably at a level of at most 95 wt %, particularly preferably at most 70 wt %.

In the catalyst to be used in the present invention, the Group 4 element may be Ti, Zr or Hf, the Group 5 element may be V, Nb or Ta, and the Group 13 element may be B, Al, Ga, In and Tl. As the Group 4 element, each of Ti, Zr and Hf is preferred, and Ti or Zr is particularly preferred. As the Group 5 element, V, Nb or Ta is preferred, and as the Group 13 element, B or Ga is preferred.

In the catalyst to be used in the present invention, the Group 2 element may be Be, Mg, Ca, Sr, Ba or Ra, the Group 6 element may be Cr, Mo or W, the Group 12 element may be Zn, Cd or Hg, the Group 14 element may be Si, Ge, Sn or Pb, and the Group 15 element may be P, As, Sb or Bi. As the Group 2 element, Ba is preferred, as the Group 6 element, W is preferred, as the Group 12 element, Zn is preferred, as the Group 14 element, Si or Sn is preferred, and as the Group 15 element, P or Bi is preferred.

In the present invention, the method for preparing the catalyst is not particularly limited. For example, it may be a method wherein a halide of the above-mentioned element of Group 4, Group 5, Group 13, Group 2, Group 6, Group 12, Group 14 or Group 15, is reacted with water or an alcohol to replace a part of halogen atoms by oxygen atoms, followed by calcination to obtain halogenated oxide. It may be a method wherein oxide or hydroxide of the above-mentioned element of Group 4, Group 5, Group 13, Group 2, Group 6, Group 12, Group 14 or Group 15 is halogenated. Or it may be a method wherein this hydroxide is calcined to oxide, followed by halogenation, to obtain a catalyst.

As the method for preparing the oxide or hydroxide, there may be mentioned a method wherein an aqueous solution of a salt of the above element is hydrolyzed by aqueous ammonia or urea to a hydroxide, which is calcined to obtain an oxide, a method wherein hydroxide of the above element is kneaded and calcined to obtain oxide, a method wherein a carrier such as oxide is immersed in a solution of a salt of the above mentioned element, followed by calcination, a method wherein alkoxide of the above mentioned element is hydrolyzed, or a method wherein aqueous solution of a salt of the above-mentioned element is anodized to precipitate oxide on the anode. The calcining temperature to obtain an oxide, is from 120 to 600° C., preferably from 200 to 500° C.

As the method for halogenation, there may be mentioned a method of treating with a suitable halogenating agent, for example, a chlorofluorocarbon (CFC) such as trichlorofluoromethane (R11), dichlorodifluoromethane (R12) or trichlorotrifluoroethane (R113), a hydrochlorofluorocarbon (HCFC) such as dichlorofluoromethane (R21), chlorodifluoromethane (R22) or difluoromethane (R32), or a hydrofluorocarbon (HFC) such as 1,1,1,3-tetrafluoroethane (R134a), or treating with hydrogen chloride, hydrogen fluoride, chlorine or fluorine gas.

The conditions for the preparation of the catalyst depend upon the oxide, the hydroxide and the halogenating agent. However, usually, an excess amount of the halogenating agent is employed relative to the oxide or hydroxide. The halogenating temperature is usually from 100 to 500° C., preferably from 200 to 450° C., in a gas phase and usually from 0 to 200° C., preferably from room temperature to 120° C. in a liquid phase.

In the present invention, the reaction of 4F with R21 may be conducted in both gas phase and liquid phase systems. When the reaction is conducted in a liquid phase, it is usually preferred to conduct the reaction without solvent in order to facilitate the purification, although it is possible to conduct the reaction in an inert solvent such as perfluorooctane or perfluorobutyltetrahydrofuran.

The amount of the catalyst depends upon the catalyst used, but it is usually from 0.01 to 50 wt %, preferably from 0.1 to 10 wt %, relative to R21 in a batch reaction. The reaction temperature is usually within a temperature range from −80° C. to +200° C., preferably from −20° C. to +100° C. The reaction pressure is not particularly limited, and the reaction can be conducted under atmospheric pressure, but it is usually preferred to conduct the reaction under a slightly elevated pressure to 10 kg/cm$^2$G. The amount of 4F is usually at least equimolar to R21 in order to increase the conversion of R21.

On the other hand, if, at the time when R21 is subjected to an addition reaction to 4F in the presence of the catalyst in the present invention, the reaction is conducted under such a reaction condition that with respect to the molar ratio of 4F and R21, 4F is at least equivalent, preferably in an excess amount, to R21, disproportionation reaction of R21 can be substantially suppressed, and R225ca and R225cb can be obtained in good yield.

Chloroform formed in a small amount as a by-product by the disproportionation, will react with the excess 4F, to give 1,3,3-trichloro-1,1,2,2-tetrafluoropropane (R224ca) as shown by the following formula, and thus, such an operation is preferred.

$$CF_2=CF_2(4F)+CHCl_3(chloroform) \rightarrow CClF_2CF_2CHCl_2(R224ca)$$

R224ca differs from R225ca and R225cb in the boiling point and can easily be separated by distillation.

The amount of 4F to be added, depends also on the type and amount of the catalyst, but is usually at least equimolar relative to R21. The molar ratio of 4F and R21 is preferably $1.01 \leq 4F/R21 \leq 10$, particularly $1.01 \leq 4F/R21 \leq 5$, more preferably $1.1 \leq 4F/R21 \leq 3$.

The feeding method of 4F and R21 is not particularly limited so long as the reaction condition is such that the amount of added 4F is at least equal, preferably in excess, relative to R21. However, to suppress the disproportionation reaction of R21, it is particularly preferred to supply them continuously to the reactor while maintaining the feeding molar ratio of 4F and R21 to a level of $1 \leq 4F/R21$, preferably $1.01 \leq 4F/R21 \leq 10$, particularly $1.01 \leq 4F/R21 \leq 5$, more preferably $1.1 \leq 4F/R21 \leq 3$, and to withdraw the reaction products including R225ca and R225cb continuously from the reactor. 4F used in an excess amount can be recovered after the reaction. It may be used more than 10 molar times excess to R21, but such operation can not be economical.

The catalyst may be introduced into the reactor in advance or may continuously be supplied to the reactor with 4F and R21 and withdrawn continuously from the reactor with the reaction product containing R225ca and R225cb. In this case, the withdrawn catalyst may be recycled. If R21 is present in the reaction product, disproportionation can take place to form chloroform. Therefore, it is always preferred to minimize the concentration of R21 to improve the selectivity for the desired reaction. To minimize the concentration of R21 in the reactor, it is preferred that starting materials, R21 and 4F (and the catalyst), are continuously supplied to the reactor and the reaction product is continuously withdrawn, whereby the concentrations of the respective components can be maintained at constant levels, and if 4F is used in excess, the concentration of R21 can be suppressed at the minimum level.

As a reactor to be used for the continuous operation, a so-called continuous reactor may be used, which may be a continuous stirred tank reactor or a plug flow reactor. Further, it is necessary to charge a reaction solvent at the initiation of the reaction. However, in the case of continuous operation, the reaction solvent is gradually replaced by the reaction product as the reaction continuously proceeds. Therefore, the reaction solvent is not particularly limited so long as it does not adversely affect the main reaction.

As the initial solvent of the reaction, a perfluoro carbon (PFC) such as perfluorooctane or perfluorobutyltetrahydrofuran, a chlorofluorocarbon (CFC) such as 1,1,1-trichloropentafluoropropane (R215cb), 1,1,3-trichloropentafluoropropane (R215ca) or 1,1,1,3-tetrachlorotetrafluoropropane (R214cb), or a hydrochlorofluorocarbon (HCFC) such as R225ca, R225cb or R224ca, may, for example, be suitable. However, it is of course possible to conduct the reaction without any solvent.

In the continuous operation, the reaction is conducted usually at a reaction temperature within a range of from $-80°$ C. to $+200°$ C., preferably from $-20°$ C. to $+100°$ C., and the reaction pressure is usually from 0 to 20 kg/cm$^2$G, preferably from 0 to 10 kg/cm$^2$G.

In the case of continuous operation, the residence time of the reaction solution depends also on either the reaction temperature or the type of the catalyst, but is usually from 0.1 minute to 24 hours, preferably from 1 minute to 10 hours. The amount of the catalyst is usually from 0.1 to 50 mol %, preferably from 0.1 to 10 mol %, relative to R21.

In a case where the reaction is conducted in a fixed bed, the catalyst is packed in a predetermined amount, and then 4F and R21 are allowed to flow at a predetermined molar ratio and at a predetermined linear velocity. The crude reaction product obtained from the outlet of the tube reactor, is recovered and then treated by a usual purification method such as distillation to obtain desired R225ca and R225cb. When the reaction is conducted in a liquid phase, an inert solvent such as perfluorooctane or perfluorobutyltetrahydrofuran, or R225ca or R225cb, may be allowed to flow together with 4F and R21. When the reaction is conducted in a gas phase, only 4F and R21 may be allowed to flow.

The amount of 4F to be added also depends on the type of the catalyst, but is usually at least equimolar relative to R21. Preferably, the molar ratio of 4F and R21 is $1.01 \leq 4F/R21 \leq 10$, particularly $1.01 \leq 4F/R21 \leq 5$, more preferably $1.1 \leq 4F/R21 \leq 3$. The reaction is conducted usually at a reaction temperature within a range of from $-80°$ C. to $+200°$ C., preferably from $-20°$ C. to $+100°$ C., and the reaction pressure is not particularly limited. An adequate reaction takes place even under atmospheric pressure, but in order to increase the reaction efficiency, it is possible to conduct the reaction under an elevated pressure. If the reaction is conducted at a reaction temperature of at least 60° C. under atmospheric pressure, it is possible to recover the product in a gas state.

BEST MODE FOR CARRYING OUT THE INVENTION

Now, Examples of the present invention will be described. Firstly, Preparation Examples for the catalysts will be shown.

PREPARATION EXAMPLE 1

1,000 g of zirconium oxide obtained by the preparation from an aqueous solution of zirconium nitrate and aqueous ammonia, followed by calcination, was dried at 250° C. Then, 3 kg of R11 diluted with nitrogen gas was added to halogenate the oxide.

PREPARATION EXAMPLE 2

1,000 g of titanium oxide obtained by the preparation from an aqueous solution of titanium tetrachloride and aqueous ammonia, followed by calcination, was dried at 180°. Then, 3 kg of R11 diluted with nitrogen gas was added to halogenate the oxide.

PREPARATION EXAMPLE 3

1,000 g of commercially available gallium oxide was dried at 250° C. Then, 1 kg of HF diluted with nitrogen was added, and 2 kg of R11 was further added, for chlorination and fluorination.

PREPARATION EXAMPLE 4

An aqueous solution of AlCl$_3$ (50 g) in 2 l of hydrochloric acid, was impregnated to 1,000 g of zirconium oxide, followed by drying to remove moisture. The product was chlorinated and fluorinated at 250° C. in a stream of a gas mixture of R11/N$_2$ and thus activated. The amount of R11 used was 3 kg.

PREPARATION EXAMPLE 5

A catalyst was prepared and activated in the same manner as in Preparation Example 4 except that 1,000 g of titanium oxide was used instead of zirconium oxide and the chlorination and fluorination were conducted at 180° C. in a stream of a gas mixture of R11/N$_2$.

PREPARATION EXAMPLE 6

A catalyst was prepared and activated in the same manner as in Preparation Example 4 except that 1,000 g of gallium oxide was used instead of zirconium oxide and the chlorination and fluorination were conducted at 250° C. in a stream of a gas mixture of R11/N$_2$.

PREPARATION EXAMPLE 7

A catalyst was prepared and activated in the same manner as in Preparation Example 4 except that 1,000 g of silicon oxide was used instead of zirconium oxide and the chlorination and fluorination were conducted at 180° C. in a stream of a gas mixture of R11/N$_2$.

PREPARATION EXAMPLE 8

A solution of GaCl$_3$ (176 g) in 200 g of water cooled with ice and a solution of concentrated sulfuric acid (4 ml) and ammonium sulfate (210 g) in 320 ml of water, were added to a solution of TiCl$_4$ (190 g) in 300 ml of water while cooling with ice. The solution was heated for one hour on a hot water bath, and 400 ml of 30% aqueous ammonia was added thereto to obtain a coprecipitate. It was further heated for one hour, and then the precipitate was collected by filtration, dried and calcined at 500° C. for 3 hours to obtain Ga$_2$O$_3$—TiO$_2$. This was fluorinated at 250° C. in a stream of a gas mixture of HF/N$_2$ and then further chlorinated and fluorinated at 200° C. in a stream of R11 gas. HF and R11 used, were 150 g and 300 g, respectively.

PREPARATION EXAMPLE 9

$Ga_2O_3$—$ZrO_2$ was obtained in the same manner as in Preparation Example 8 except that 340 g of $Zr(NO_3)_4$ was used instead of 190 g of $TiCl_4$. This was fluorinated at 200° C. in a stream of a gas mixture of $HF/N_2$ and then further chlorinated and fluorinated at 180° C. in a stream of R11 gas. HF and R11 used, were 150 g and 300 g, respectively.

PREPARATION EXAMPLE 10

A solution of 82 g of $ZnCl_2$, 4 ml of concentrated sulfuric acid and 210 g of ammonium sulfate in 320 ml of water, was added to a solution of 136 g of $AlCl_3$ in 300 ml of water while cooling with ice. The solution was heated for one hour on a hot water bath, and 400 ml of 30% aqueous ammonia was added thereto to precipitate a coprecipitate. This was further heated for one hour, and then the precipitate was collected by filtration, dried and calcined at 500° C. for 3 hours to obtain $Al_2O_3$—$ZnO$. This was fluorinated at 250° C. in a stream of a gas mixture of $HF/N_2$ and then further chlorinated and fluorinated at 250° C. in a stream of R11 gas. HF and R11 used, were 150 g and 300 g, respectively.

PREPARATION EXAMPLE 11

A solution of niobium pentaethoxide (50 g) in 2 l of ethanol, was impregnated to 1,000 g of commercially available γ-alumina, followed by drying to remove the solvent, and the product was further calcined at 600° C. Then, the product was chlorinated and fluorinated at 250° C. in a stream of a gas mixture of $R11/N_2$ and thus activated. R11 used, was 3 kg.

PREPARATION EXAMPLE 12

A solution of tantalum pentaethoxide (50 g) in 2 l of ethanol, was impregnated to 1,000 g of commercially available γ-alumina, followed by drying to remove the solvent. Further, the product was calcined at 600° C. Then, it was chlorinated and fluorinated at 250° C. in a stream of a gas mixture of $R11/N_2$ and thus activated. R11 used, was 3 kg.

PREPARATION EXAMPLE 13

1,000 g of commercially available γ-alumina was dried, and then chlorinated and fluorinated at 250° C. in a stream of a gas mixture of $R11/N_2$. R11 used, was 3 kg.

PREPARATION EXAMPLE 14

A catalyst was prepared and activated in the same manner as in Preparation Example 4 except that 1,000 g of commercially available γ-alumina was used instead of zirconium oxide and the chlorination and fluorination were conducted at from 150 to 400° C. in a stream of a gas mixture of $R11/N_2$.

PREPARATION EXAMPLE 15

Activated carbon was immersed in pure water to let water penetrate into the interior of pores. $AlCl_3$ was gradually dropwise added thereto in a form of an aqueous solution having 0.5% thereof dissolved as the total weight of the metal component to the weight of the active carbon, to have the ion component adsorbed on the activated carbon. Then, it was washed with pure water and then dried at 150° C. for 5 hours. Then, it was kept at 250° C. for 4 hours in nitrogen atmosphere and was chlorinated and fluorinated at 250° C. in a stream of $R11/N_2$ gas. The amount of R11 used, was 1 kg.

PREPARATION EXAMPLE 16

1,000 g of zirconium oxide obtained from an aqueous zirconyl oxychloride and aqueous ammonia, followed by calcination at 400° C., was dried and then chlorinated and fluorinated at 250° C. in a gas stream of $R11/N_2$, to obtain halogenated oxide. The amount of R11 used, was 6 kg.

PREPARATION EXAMPLE 17

Complex oxide was obtained from an aqueous solution of 2,400 g of zirconyl nitrate and 375 g of aluminum nitrate and aqueous ammonia. The product was dried, then chlorinated and fluorinated at 250° C. in a stream of a gas mixture of $R11/N_2$. The amount of R11 used, was 6 kg.

PREPARATION EXAMPLE 18

Complex oxide was obtained from an aqueous solution of 1,850 g of zirconyl nitrate and 1,110 g of aluminum nitrate and aqueous ammonia, followed by calcination. The product was dried, and then chlorinated and fluorinated at from 200 to 450° C. in a stream of a gas mixture of $R12/R32/N_2$. The amounts of R12 and R32 used, were 5 kg and 1 kg, respectively.

PREPARATION EXAMPLE 19

Complex oxide was obtained from an aqueous solution of 970 g of zirconyl nitrate and 2,040 g of aluminum nitrate and aqueous ammonia, followed by calcination. The product was dried, and then chlorinated and fluorinated at a temperature of 250 to 300° C. in a stream of a gas mixture of $HF/Cl_2/N_2$. The amounts of HF and $Cl_2$ used, were 3 kg and 1 kg, respectively.

PREPARATION EXAMPLE 20

Oxide was obtained by dropwise adding 2,000 g of titanium tetrachloride to 10 l of dilute hydrochloric acid, then adding aqueous ammonia thereto, and calcining the product at 400° C. The product was chlorinated and fluorinated at 200° C. in a stream of a gas mixture of $R11/N_2$. The amount of R11 used, was 6 kg.

PREPARATION EXAMPLE 21

Composite oxide was obtained by adding 1,200 g of zirconyl nitrate and 850 g of titanium tetrachloride to dilute hydrochloric acid, then further adding aqueous ammonia thereto, and calcining the product. The product was dried and then chlorinated and fluorinated at 200° C. in a stream of a gas mixture of $R11/N_2$. The amount of R11 used, was 6 kg.

PREPARATION EXAMPLE 22

Composite oxide was obtained from an aqueous solution of 2,000 g of zirconyl nitrate and 108 g of hafnium oxychloride and aqueous ammonia, followed by calcination. The product was dried and then chlorinated and fluorinated at 250° C. in a stream of a gas mixture of $R11/+N_2$. The amount of R11 used, was 6 kg.

PREPARATION EXAMPLE 23

Composite oxide was obtained from an aqueous solution of 2,000 g of zirconyl nitrate and 96 g of barium chloride and aqueous ammonia, followed by calcination. The product was chlorinated and fluorinated at 250° C. in a stream of a gas mixture of $HF/Cl_2/N_2$. The amounts of HF and $Cl_2$ used, were 3 kg and 1 kg, respectively.

PREPARATION EXAMPLE 24

Composite oxide was obtained by dissolving 2,000 g of zirconyl nitrate and 190 g of bismuth nitrate in an aqueous nitric acid solution, followed by evaporation to dryness and calcination. The product was dried and then chlorinated and fluorinated at 250° C. in a stream of a gas mixture of $R11/N_2$. The amount of R11 used, was 6 kg.

PREPARATION EXAMPLE 25

Composite oxide was obtained by the preparation from an aqueous solution of 2,000 g of zirconyl nitrate and 140 g of stannic chloride and aqueous ammonia, followed by calcination. The product was dried and then chlorinated and fluorinated at 250° C. in a stream of a gas mixture of $R11/N_2$. The amount of R11 used, was 6 kg.

PREPARATION EXAMPLE 26

Composite oxide was prepared by adding 2,000 g of titanium tetrachloride and 140 g of stannic chloride to an aqueous hydrochloric acid solution and then adding aqueous ammonia, followed by calcination. The product was dried and then chlorinated and fluorinated at 200° C. in a stream of a gas mixture of $R21/N_2$. The amount of R11 used, was 6 kg.

PREPARATION EXAMPLE 27

Composite oxide was obtained by evaporating an aqueous nitric acid solution of 2,000 g of zirconyl nitrate and 190 g of ammonium tungstate to dryness, followed by calcination. The product was dried and then chlorinated and fluorinated at 250° C. in a stream of a gas mixture of $R11/N_2$. The amount of R11 used, was 6 kg.

PREPARATION EXAMPLE 28

Composite oxide was obtained from an aqueous solution of 2,000 g of zirconyl nitrate and 155 g of gallium nitrate and aqueous ammonia, followed by calcination. The product was dried and then chlorinated and fluorinated at a temperature of from 250 to 450° C. in a stream of a gas mixture of $R11/N_2$. The amount of R11 used, was 6 kg.

PREPARATION EXAMPLE 29

Composite oxide was obtained from an aqueous oxalic acid solution of 2,000 g of zirconyl nitrate and 100 g of ammonium metavanadate, followed by calcination. The product was dried and then chlorinated and fluorinated at 250° C. in a stream of a gas mixture of $R12/N_2$. The amount of R12 used, was 6 kg.

PREPARATION EXAMPLE 30

Composite oxide was obtained from an aqueous solution of 2,000 g of zirconyl nitrate and 50 g of boric acid, followed by calcination. The product was dried and then chlorinated and fluorinated at 250° C. in a stream of a gas mixture of $R11/N_2$. The amount of R11 used, was 6 kg.

PREPARATION EXAMPLE 31

Composite oxide was obtained from an aqueous solution of 1,000 g of zirconyl oxychloride and 760 g of ammonium phosphate and aqueous ammonia, followed by calcination. The product was dried and then chlorinated and fluorinated at 250° C. in a stream of a gas mixture of $R12/N_2$. The amount of R12 used, was 6 kg.

PREPARATION EXAMPLE 32

Composite oxide was obtained from a dilute hydrochloric acid solution of 2,000 g of titanium tetrachloride and an aqueous solution of 70 g of boric acid, followed by calcination. The product was dried and then chlorinated and fluorinated at 200° C. in a stream of a gas mixture of $R11/N_2$. The amount of R11 used, was 6 kg.

PREPARATION EXAMPLE 33

Composite oxide was obtained from a dilute hydrochloric acid solution of 1,000 g of titanium tetrachloride, an aqueous solution of 510 g of orthophosphoric acid and aqueous ammonia, followed by calcination. The product was dried and then chlorinated and fluorinated at 200° C. in a stream of a gas mixture of $R12/N_2$. The amount of R12 used, was 6 kg.

PREPARATION EXAMPLE 34

Complex oxide was obtained from an aqueous solution of 1,850 g of zirconyl nitrate and 1,110 g of aluminum nitrate and aqueous ammonia, followed by calcination. The product was dried and then chlorinated and fluorinated at a temperature of from 50 to 250° C. in a stream of a gas mixture of $HCl/F_2$ gas/$N_2$ and then further chlorinated and fluorinated at 250° C. in a stream of a gas mixture of $R12/N_2$. The amounts of HCl, $F_2$ gas and R12 were 1 kg, 200 g and 4 kg, respectively.

PREPARATION EXAMPLE 35

Hydroxide was prepared from an aqueous solution of 1850 g of zirconyl nitrate and 1,110 g of aluminum nitrate and aqueous ammonia, and calcination and chlorination-fluorination were simultaneously conducted at a temperature of from 200 to 400° C. under a stream of a gas mixture of $R12/N_2$. The amount of R12 used, was 7 kg.

Now, reaction examples using the above catalysts will be given as Examples and Comparative Examples.

EXAMPLES 1 TO 12 AND COMPARATIVE EXAMPLES 1 TO 3

Into a 1 l autoclave made of Hastelloy C, 50 g of the catalyst prepared by the method in one of Preparation Examples 1 to 12, was added, and after deaeration under reduced pressure, 500 g (3.64 mol) of R21 was added. While maintaining the autoclave at 0° C., 4F was continuously added. After adding 400 g (4 mol) of 4F, the autoclave was kept stirring for one more hour. Then, the reaction solution was filtered to obtain 800 g of the crude reaction solution and analyzed by gas chromatography and 19F-NMR. The results of analyses of the composition of the reaction solution (unit: mol %) are shown in Table 1 (Examples 1 to 9) and Table 2 (Examples 10 to 12). Also, the results of the reaction using the catalysts prepared by the method in Preparation Examples 13 to 15 are shown in Table 2 (Comparative Examples 1 to 3).

TABLE 1

| | Example No. | | | | | | | | |
|---|---|---|---|---|---|---|---|---|---|
| | 1 | 2 | 3 | 4 | 5 | 6 | 7 | 8 | 9 |
| | Preparation Example No. | | | | | | | | |
| | 1 | 2 | 3 | 4 | 5 | 6 | 7 | 8 | 9 |
| R225ca | 20 | 18 | 13 | 21 | 20 | 15 | 9 | 23 | 20 |
| R225cb | 37 | 36 | 22 | 38 | 35 | 21 | 15 | 33 | 38 |
| R225aa | <0.1 | <0.1 | <0.1 | <0.1 | <0.1 | <0.1 | <0.1 | <0.1 | <0.1 |
| R225ba | <0.1 | <0.1 | <0.1 | <0.1 | <0.1 | <0.1 | <0.1 | <0.1 | <0.1 |
| $CHCl_3$ | 31 | 30 | 48 | 28 | 33 | 48 | 68 | 31 | 27 |
| R224ca | 7 | 10 | 13 | 10 | 9 | 13 | 4 | 8 | 9 |
| Other | 5 | 6 | 4 | 3 | 3 | 3 | 4 | 5 | 6 |

TABLE 2

| | Example No. | | | | | |
|---|---|---|---|---|---|---|
| | 10 | 11 | 12 | Comparative Example 1 | Comparative Example 2 | Comparative Example 3 |
| | Preparation Example No. | | | | | |
| | 10 | 11 | 12 | 13 | 14 | 15 |
| R225ca | 30 | 25 | 25 | 26 | 32 | 31 |
| R225cb | 29 | 38 | 41 | 22 | 23 | 22 |
| R225aa | <0.1 | 0.2 | 0.2 | 3 | 3 | 3 |
| R225ba | <0.1 | 0.1 | 0.1 | 1 | 1 | 1 |
| $CHCl_3$ | 27 | 25 | 24 | 36 | 31 | 31 |
| R224ca | 10 | 10 | 8 | 9 | 7 | 7 |
| Other | 4 | 1.7 | 1.7 | 3 | 3 | 5 |

EXAMPLES 13 TO 32

Into a 200 ml autoclave made of Hastelloy C, 10 g of the catalyst prepared by the Preparation Example as identified in the following Tables 3 to 5, was added, and after deaeration under reduced pressure, 25 g (0.25 mol) of R21 and 30 g (0.3 mol) of 4F were added.

Then, the mixture was stirred for one hour in an ice bath, and every thirty minutes, 10 g of R21 and 12 g of 4F were added, and the reaction was continued. The feed materials were added until the total charged amount of R21 and 4F came to 105 g (1 mol) and 126 g (1.3 mol) respectively. After stirring the mixture for one hour, the reaction solution was filtered to recover a crude reaction solution. It was analyzed by means of gas chromatography (GC) and NMR. The results are shown in Table 3 (Examples 13 to 19), Table 4 (Examples 20 to 26) and Table 5 (Examples 27 to 32).

TABLE 3

| | Example No. | | | | | | |
|---|---|---|---|---|---|---|---|
| | 13 | 14 | 15 | 16 | 17 | 18 | 19 |
| | Preparation Example No. | | | | | | |
| | 16 | 17 | 18 | 19 | 20 | 21 | 22 |
| Recovered crude solution (g) | 185 | 184 | 185 | 183 | 185 | 185 | 184 |
| R21 conversion (%) | 100 | 100 | 100 | 100 | 100 | 100 | 100 |
| R225ca selectivity (%) | 29 | 33 | 34 | 34 | 23 | 34 | 29 |
| R225cb selectivity (%) | 61 | 58 | 58 | 56 | 68 | 59 | 61 |
| R225aa selectivity (%) | <0.1 | <0.1 | <0.1 | <0.1 | <0.1 | <0.1 | <0.1 |
| R225ba selectivity (%) | <0.1 | <0.1 | <0.1 | <0.1 | <0.1 | <0.1 | <0.1 |
| $CHCl_3$ selectivity (%) | 1 | 1 | 1 | 1 | 1 | 1 | 1 |

TABLE 3-continued

| | Example No. | | | | | | |
|---|---|---|---|---|---|---|---|
| | 13 | 14 | 15 | 16 | 17 | 18 | 19 |
| | Preparation Example No. | | | | | | |
| | 16 | 17 | 18 | 19 | 20 | 21 | 22 |
| R224ca selectivity (%) | 8 | 7 | 6 | 8 | 7 | 5 | 8 |
| Other selectivity (%) | 1 | 1 | 1 | 1 | 1 | 1 | 1 |

TABLE 4

| | Example No. | | | | | | |
|---|---|---|---|---|---|---|---|
| | 20 | 21 | 22 | 23 | 24 | 25 | 26 |
| | Preparation Example No. | | | | | | |
| | 23 | 24 | 25 | 26 | 27 | 28 | 29 |
| Recovered crude solution (g) | 185 | 182 | 183 | 185 | 184 | 185 | 184 |
| R21 conversion (%) | 98 | 100 | 100 | 100 | 100 | 100 | 100 |
| R225ca selectivity (%) | 37 | 28 | 31 | 22 | 27 | 28 | 29 |
| R225cb selectivity (%) | 55 | 62 | 62 | 69 | 62 | 65 | 62 |
| R225aa selectivity (%) | <0.1 | <0.1 | <0.1 | <0.1 | <0.1 | <0.1 | <0.1 |
| R225ba selectivity (%) | <0.1 | <0.1 | <0.1 | <0.1 | <0.1 | <0.1 | <0.1 |
| $CHCl_3$ selectivity (%) | 1 | 1 | 1 | 1 | 1 | 1 | 1 |
| R224ca selectivity (%) | 6 | 8 | 5 | 7 | 9 | 5 | 7 |
| Other selectivity (%) | 1 | 1 | 1 | 1 | 1 | 1 | 1 |

TABLE 5

| | Example No. | | | | | |
|---|---|---|---|---|---|---|
| | 27 | 28 | 29 | 30 | 31 | 32 |
| | Preparation Example | | | | | |
| | 30 | 31 | 32 | 33 | 34 | 35 |
| Recovered crude solution (g) | 182 | 181 | 180 | 185 | 183 | 182 |
| R21 conversion (%) | 100 | 100 | 100 | 100 | 100 | 100 |
| R225ca selectivity (%) | 25 | 27 | 23 | 24 | 33 | 34 |
| R225cb selectivity (%) | 66 | 65 | 69 | 69 | 58 | 59 |
| R225aa selectivity (%) | <0.1 | <0.1 | <0.1 | <0.1 | <0.1 | <0.1 |
| R225ba selectivity (%) | <0.1 | <0.1 | <0.1 | <0.1 | <0.1 | <0.1 |
| $CHCl_3$ selectivity (%) | 1 | 1 | 1 | 1 | 1 | 1 |
| R224ca selectivity (%) | 7 | 6 | 6 | 5 | 7 | 5 |
| Other selectivity (%) | 1 | 1 | 1 | 1 | 1 | 1 |

EXAMPLE 33

A 10 l autoclave made of Hastelloy C was evacuated, and then, 10 kg of R225ca was charged as an initial solvent together with 100 g of the catalyst prepared by the method in Preparation Example 1. The reaction temperature was cooled to −5° C., and then 1,110 g/hr of 4F, 1,030 g/hr of R21 and 20 g/hr of the catalyst prepared in Preparation Example 1 were continuously added while maintaining the reaction temperature at a level of from 0 to +5° C. The reaction was conducted while continuously withdrawing the reaction mixture in the same amount as the charged amount. The composition (mol %) of the distilled solution after 30 hours is shown in Table 6. 19.7 kg of the crude reaction solution recovered after 20 hours was purified by distillation, whereby 17.5 kg of a R225 mixture (sum of R225ca, R225cb, R225aa and R225ba, the same applies hereinafter) was obtained (yield based on R21: 87%, the same applies hereinafter).

EXAMPLE 34

The reaction was conducted in the same manner as in Example 33 except that the catalyst was changed to the one prepared in Preparation Example 2. The results are shown in Table 6. 19.3 kg of the crude reaction solution recovered after 20 hours was purified by distillation to obtain 17.2 kg of a R225 mixture (yield: 86%).

EXAMPLE 35

The reaction was conducted in the same manner as in Example 33 except that the catalyst was changed to the one prepared in Preparation Example 3. The results are shown in Table 6. 19.5 kg of the crude reaction solution recovered after 20 hours, was purified by distillation to obtain 17.5 kg of a R225 mixture (yield: 87%).

EXAMPLE 36

The reaction was conducted in the same manner as in Example 33 except that the catalyst was changed to the one prepared in Preparation Example 9. The results are shown in Table 6. 19.7 kg of the crude reaction solution recovered after 20 hours, was purified by distillation to obtain 17.8 kg of a R225 mixture (yield: 88%).

EXAMPLE 37

The reaction was conducted in the same mariner as in Example 33 except that the catalyst was changed to the one prepared in Preparation Example 10. The results are shown in Table 6. 19.5 kg of the crude reaction solution recovered after 20 hours, was purified by distillation to obtain 17.6 kg of a R225 mixture (yield: 87%).

COMPARATIVE EXAMPLE 4

The reaction was conducted in the same manner as in Example 33 except that the catalyst was changed to the one prepared in Prepared Example 13. The results are shown in Table 6. 19.3 kg of the crude reaction solution recovered after 20 hours, was purified by distillation to obtain 17 kg of a R225 mixture (yield: 85%).

TABLE 6

| | Example No. | | | | | |
|---|---|---|---|---|---|---|
| | 33 | 34 | 35 | 36 | 37 | Comparative Example 4 |
| | Preparation Example No. | | | | | |
| | 1 | 2 | 3 | 9 | 10 | 13 |
| R225ca | 34 | 32 | 36 | 32 | 48 | 51 |
| R225cb | 63 | 64 | 59 | 64 | 47 | 40 |
| R225aa | <0.1 | <0.1 | <0.1 | <0.1 | <0.1 | 3 |
| R225ba | <0.1 | <0.1 | <0.1 | <0.1 | <0.1 | 1 |
| CHCl$_3$ | 0 | 0 | 1 | 0 | 0 | 0 |
| R224ca | 2 | 3 | 3 | 2 | 3 | 2 |
| Other | 1 | 1 | 1 | 2 | 2 | 3 |

EXAMPLE 38

Into a 10 l autoclave made of Hastelloy C, 0.4 kg of the catalyst prepared in Preparation Example 16 was added, and after deaeration under reduced pressure, 10 kg of R225cb was added as an initial solvent. The autoclave was cooled to −10° C., and 1,200 g/hr of 4F, 1,030 g/hr of R21 and 50 g/hr of the catalyst prepared in Preparation Example 16 were continuously added, while maintaining the reaction temperature at a level of from 0 to +10° C. The reaction was conducted while continuously withdrawing the reaction mixture in the same amount as the charged amount. The composition of the reaction solution after 40 hours is shown in Table 7. 84 kg of the crude reaction solution recovered, was purified by distillation to obtain 81 kg of a R225 mixture (yield: 95%).

EXAMPLE 39

The reaction was conducted in the same manner as in Example 38 except that the catalyst prepared in Preparation Example 17 was used. The composition of the reaction solution after 40 hours is shown in Table 7. 85 kg of the crude reaction solution recovered, was purified by distillation to obtain 81 kg of a R225 mixture (yield: 95%).

EXAMPLE 40

The reaction was conducted in the same manner as in Example 38 except that the catalyst prepared in Preparation Example 20 was used. The composition of the reaction solution after 40 hours is shown in Table 7. 85 kg of the crude reaction solution recovered, was purified by distillation to obtain 81 kg of a R225 mixture (yield: 95%).

EXAMPLE 41

The reaction was conducted in the same manner as in Example 38 except that the catalyst prepared in Preparation Example 31 was used. The composition of the reaction solution after 40 hours is shown in Table 7. 83 kg of the crude reaction solution recovered, was purified by distillation to obtain 80 kg of a R225 mixture (yield: 95%).

EXAMPLE 42

Into a tube reactor made of Inconel having an inner diameter of ½ inch, 50 ml of the catalyst prepared in Preparation Example 16 was charged. After purging with N$_2$ gas, the tube reactor was placed in a water bath of +10° C., and 100 ml/min of 4F and 50 ml/min of R21 were fed. The outlet of the tube reactor was maintained at 100° C. to gasify all the reaction product. After two hours, the crude gas from the outlet of the tube reactor was analyzed by means of gas chromatography and 19F-NMR. The results are shown in Table 7.

EXAMPLE 43

The reaction was conducted in the same manner as in Example 42 except that the reaction temperature was changed to +50° C. The results are shown in Table 7.

EXAMPLE 44

The reaction was conducted in the same manner as in Example 42 except that the catalyst prepared in Preparation Example 20 was used. The results are shown in Table 7.

EXAMPLE 45

The reaction was conducted in the same manner as in Example 42 except that the catalyst prepared in Preparation Example 21 was used. The results are shown in Table 7.

TABLE 7

|  | Example No. | | | | | | | |
| --- | --- | --- | --- | --- | --- | --- | --- | --- |
|  | 38 | 39 | 40 | 41 | 42 | 43 | 44 | 45 |
|  | Preparation Example | | | | | | | |
|  | 16 | 17 | 20 | 31 | 16 | 16 | 20 | 21 |
| R21 conversion (%) | 100 | 100 | 100 | 100 | 100 | 100 | 100 | 100 |
| R225ca selectivity (%) | 26 | 28 | 18 | 22 | 26 | 28 | 18 | 20 |
| R225cb selectivity (%) | 72 | 70 | 79 | 76 | 72 | 69 | 79 | 77 |
| R225aa selectivity (%) | <0.1 | <0.1 | <0.1 | <0.1 | <0.1 | <0.1 | <0.1 | <0.1 |
| R225ba selectivity (%) | <0.1 | <0.1 | <0.1 | <0.1 | <0.1 | <0.1 | <0.1 | <0.1 |
| $CHCl_3$ selectivity (%) | 0 | 0 | 0 | 0 | 0 | 1 | 0 | 1 |
| R224ca selectivity (%) | 1 | 1 | 2 | 1 | 1 | 1 | 2 | 1 |
| Other selectivity (%) | 1 | 1 | 1 | 1 | 1 | 1 | 1 | 1 |

What is claimed is:

1. A method for producing 3,3-dichloro-1,1,1,2,2-pentafluoropropane and 1,3-dichloro-1,1,2,2,3-pentafluoropropane, which comprises reacting tetrafluoroethylene with dichlorofluoromethane in the presence of a catalyst comprising a halogenated oxide containing at least one element selected from the group consisting of Ti, Zr, Hf, V, Nb, Ta, B, Ga, In and Tl.

2. The method of claim 1, wherein said catalyst further comprises halogenated aluminum oxide.

3. The method of claim 1, wherein said catalyst further comprises a halogenated oxide of at least one element selected from the group consisting of Group 2, Group 6, Group 12, Group 14 and Group 15.

4. The method of claim 1, wherein said catalyst is a halogenated oxide containing at least one element selected from the group consisting of Ti, Zr, Hf, V, B and Ga.

5. The method of claim 1, wherein the temperature of the reaction of tetrafluoroethylene with dichlorofluoromethane is from −80° C. to +200° C.

6. The method of claim 1, wherein tetrafluoroethylene and dichlorofluoromethane are reacted at a tetrafluoroethylene/dichlorofluoromethane ratio of at least 1.

7. The method of claim 4, wherein said catalyst further comprises a halogenated oxide containing at least one element selected from the group consisting of Ba, W, Zn, Si, Sn, Bi and P.

8. A method for producing 3,3-dichloro-1,1,1,2,2-pentafluoropropane and 1,3-dichloro-1,1,2,2,3-pentafluoropropane, which comprises reacting tetrafluoroethylene with dichlorofluoromethane in the presence of a catalyst comprising a halogenated oxide containing at least one element selected from the group consisting of Ti, Zr and Hf.

9. The method of claim 8, wherein said catalyst further comprises halogenated aluminum oxide.

10. The method of claim 8, wherein said catalyst further comprises a halogenated oxide of at least one element selected from the group consisting of Group 2, Group 6, Group 12, Group 14 and Group 15.

11. The method of claim 8, wherein the temperature of the reaction of tetrafluoroethylene with dichlorofluoromethane is from −80° C. to +200° C.

12. The method of claim 8, wherein tetrafluoroethylene and dichlorofluoromethane are reacted at a tetrafluoroethylene/dichlorofluoromethane ratio of at least 1.

13. The method of claim 8, wherein said catalyst further comprises a halogenated oxide containing at least one element selected from the group consisting of Ba, W, Zn, Si, Sn, Bi and P.

14. A method for producing 3,3-dichloro-1,1,1,2,2-pentafluoropropane and 1,3-dichloro-1,1,2,2,3-pentafluropropane, which comprises reacting tetrafluoroethylene with dichlorofluoromethane in the presence of a catalyst comprising a halogenated oxide containing at least one element selected from the group consisting of V, Nb and Ta.

15. The method of claim 14, wherein said catalyst further comprises halogenated aluminum oxide.

16. The method of claim 14, wherein said catalyst further comprises a halogenated oxide of at least one element selected from the group consisting of Group 2, Group 6, Group 12, Group 14 and Group 15.

17. The method of claim 14, wherein said catalyst is a halogenated oxide containing V.

18. The method of claim 14, wherein the temperature of the reaction of tetrafluoroethylene with dichlorofluoromethane is from −80° C. to +200° C.

19. The method of claim 14, wherein tetrafluoroethylene and dichlorofluoromethane are reacted at a tetrafluoroethylene/dichlorofluoromethane ratio of at least 1.

20. The method of claim 17, wherein said catalyst further comprises a halogenated oxide containing at least one element selected from the group consisting of Ba, W, Zn, Si, Sn, Bi and P.

21. A method for producing 3,3-dichloro-1,1,1,2,2-pentafluoropropane and 1,3-dichloro-1,1,2,2,3-pentafluropropane, which comprises reacting tetrafluoroethylene with dichlorofluoromethane in the presence of a catalyst comprising a halogenated oxide containing at least one element selected from the group consisting of B, Ga, In and Tl.

22. The method of claim 21, wherein said catalyst further comprises halogenated aluminum oxide.

23. The method of claim 21, wherein said catalyst further comprises a halogenated oxide of at least one element selected from the group consisting of Group 2, Group 6, Group 12, Group 14 and Group 15.

24. The method of claim 21 wherein said catalyst is a halogenated oxide containing at least one element selected from the group consisting of B and Ga.

25. The method of claim 21, wherein the temperature of the reaction of tetrafluoroethylene with dichlorofluoromethane is from −80° C. to +200° C.

26. The method of claim 21 wherein tetrafluoroethylene and dichlorofluoromethane are reacted at a tetrafluoroethylene/dichlorofluoromethane ratio of at least 1.

27. The method of claim 24, wherein said catalyst further comprises a halogenated oxide containing at least one element selected from the group consisting of Ba, W, Zn, Si, Sn, Bi and P.

28. The method of claim 1, wherein said catalyst is represented by the formula (1)

$$MX_pO_q \qquad (1)$$

wherein

M is at least one element selected from the group consisting of Ti, Zr, Hf, V, Nb, Ta, B, Ga, In and Tl;

X is at least one element selected from the group consisting of F, Cl, Br and I; and $0<p<5$, $0<q<2.5$ and $3 \leq p+2q<8$.

29. The method of claim 1 wherein an amount of 2,2-dichloro-1,1,1,3,3-pentafluoropropane and 2,3-dichloro-1,1,1,2,3-pentafluoropropane produced is less than an amount produced by using a halogenated aluminum oxide catalyst alone.

* * * * *